United States Patent
Christians et al.

(10) Patent No.: US 11,191,713 B2
(45) Date of Patent: Dec. 7, 2021

(54) OIL IN WATER EMULSION

(71) Applicant: Dr. August Wolff GmbH & Co. KG Arzneimittel, Bielefeld (DE)

(72) Inventors: Thorsten Christians, Bielefeld (DE); Ulrich Knie, Bielefeld (DE); Christoph Abels, Bielefeld (DE)

(73) Assignee: Dr. August Wolff GmbH & Co. KG Arzneimittel, Bielefeld (DE)

( * ) Notice: Subject to any disclaimer, the term of this patent is extended or adjusted under 35 U.S.C. 154(b) by 207 days.

(21) Appl. No.: 16/611,165

(22) PCT Filed: Jul. 16, 2018

(86) PCT No.: PCT/EP2018/069273
§ 371 (c)(1),
(2) Date: Nov. 5, 2019

(87) PCT Pub. No.: WO2019/016139
PCT Pub. Date: Jan. 24, 2019

(65) Prior Publication Data
US 2020/0101005 A1 Apr. 2, 2020

(30) Foreign Application Priority Data
Jul. 17, 2017 (EP) .................................... 17181684

(51) Int. Cl.
| A61K 8/86 | (2006.01) |
| A61K 8/06 | (2006.01) |
| A61K 8/34 | (2006.01) |
| A61K 8/37 | (2006.01) |
| A61K 8/49 | (2006.01) |
| A61Q 15/00 | (2006.01) |
| A61K 47/10 | (2017.01) |
| A61K 47/14 | (2017.01) |
| A61Q 19/00 | (2006.01) |
| A61K 9/00 | (2006.01) |
| A61K 31/40 | (2006.01) |
| A61K 9/107 | (2006.01) |

(52) U.S. Cl.
CPC ................ *A61K 8/86* (2013.01); *A61K 8/062* (2013.01); *A61K 8/342* (2013.01); *A61K 8/37* (2013.01); *A61K 8/4913* (2013.01); *A61Q 15/00* (2013.01)

(58) Field of Classification Search
CPC .. A61K 2800/413; A61K 31/40; A61K 47/10; A61K 47/14; A61K 8/062; A61K 8/342; A61K 8/37; A61K 8/4913; A61K 8/86; A61K 9/0014; A61Q 15/00; A61Q 19/00
See application file for complete search history.

(56) References Cited

U.S. PATENT DOCUMENTS

| 2015/0196490 A1 | 7/2015 | Edelson et al. |
| 2016/0058735 A1* | 3/2016 | Pena ................... A61K 8/4913 424/65 |
| 2017/0087088 A1 | 3/2017 | Edelson et al. |

FOREIGN PATENT DOCUMENTS

| WO | WO 2006/069998 A2 | 7/2006 |
| WO | WO 2012/103038 A2 | 8/2012 |
| WO | WO 2014/134510 A1 | 9/2014 |

OTHER PUBLICATIONS

Search Report and Written Opinion, dated Oct. 1, 2018, corresponding to International Application No. PCT/EP2018/069273 (filed Jul. 16, 2018), 8 pp.

* cited by examiner

*Primary Examiner* — Jeffrey T. Palenik
(74) *Attorney, Agent, or Firm* — Leydig, Voit & Mayer, Ltd.

(57) ABSTRACT

The present invention relates to an oil-in-water emulsion comprising a glycopyrronium salt and an emulsifier system comprising at least one macrogol glycerol fatty acid ester, at least one glycerol fatty acid ester and at least one fatty alcohol. Moreover, the present invention relates to such an emulsion for use as a medicament, in particular for treating and preventing diseases in conjunction with excessive sweating. In addition the present invention relates to the non-therapeutic use of such an oil-in-water emulsion for topical application on the skin of a mammal in order to reduce sweating.

20 Claims, No Drawings

OIL IN WATER EMULSION

CROSS-REFERENCE TO RELATED APPLICATIONS

This application is a U.S. National Stage Application filed under 35 U.S.C. § 371 of International Application No. PCT/EP2018/069273, filed Jul. 16, 2018, which claims the benefit of European Application No. 17181684.6, filed Jul. 17, 2017. Both of these applications are hereby incorporated by reference in their entireties.

The present invention relates to an oil-in-water emulsion comprising a glycopyrronium salt (GP salt) and an emulsifier system comprising at least one macrogol glycerol fatty acid ester, at least one glycerol fatty acid ester and at least one fatty alcohol. Moreover, the present invention relates to such an emulsion for use as a medicament, in particular for treating and preventing diseases in conjunction with excessive sweating (hyperhidrosis). In addition, the present invention relates to the non-therapeutic (cosmetic) use of such an oil-in-water emulsion for topical application on the skin of a mammal in order to reduce sweating.

Excessive sweating or hyperhidrosis is a condition beyond what is physiologically required to maintain normal thermal regulation of the human body. Thus, hyperhidrosis is an extremely inconvenient condition negatively affecting daily life of a person suffering therefrom. Hyperhidrosis can be divided into focal and general primary hyperhidrosis. The focal is bilaterally symmetrical: hands, feet, axillae or groins. Focal hyperhidrosis from the face/head does occur but is often part of the general form. Generalized sweating usually involves both the head and trunk and in severe cases also extremities and groins/glutes. Whereas the majority of patients affected have the primary form which is hereditary, there is also a secondary form, often related to an underlying disease.

A variety of treatments have been proposed for treating excessive sweating/hyperhidrosis which include aluminum containing antiperspirants, surgical removal of sweat glands and systemic or local treatment with anticholinergic compounds. Any of these treatments, however, entail serious disadvantages. Aluminum containing antiperspirants, in particular upon continuous use, stain or discolor the textiles coming into contact with the antiperspirant. In addition, the increasing amount of aluminum in waste water recently has also been increasing environmental concerns. On the other hand, removal of the sweat glands means surgery that may be accompanied by at least inconvenient or even serious side effects.

As an alternative to the treatments mentioned above, glycopyrronium salts (also named glycopyrrolates) have been proposed for the treatment of excessive sweating and hyperhidrosis. WO 2006/069998 discloses the use of glycopyrronium bromide together with a large variety of other active ingredients for the treatment of excessive sweating. WO 2014/134510 relates to a specific glycopyrronium tosylate salt for the treatment of excessive sweating and hyperhidrosis. However, all of these known compositions basically suffer from at least one insufficiency selected from instability of the composition, inadequate cosmetic acceptance and skin care characteristics, systemic side effects and/or limited efficacy. WO 2012/103038, US 2015/196490 and US 2017/087088 disclose emulsions containing glycopyrrolate and a specific emulsifying agent for treating hyperhidrosis.

In view thereof there is still need in the prior art for new glycopyrronium salt containing compositions having improved properties.

Therefore, the object underlying the present invention is the provision of novel glycopyrronium salt containing compositions for the improved treatment of excessive sweating (hyperhidrosis) and in particular of primary hyperhidrosis.

This object is achieved by the provision of the oil-in-water emulsion of the present invention comprising, next to at least one glycopyrronium salt, the specific emulsifier system comprising at least one macrogol glycerol fatty acid ester, at least one glycerol fatty acid ester, and at least one fatty alcohol. In particular, it has surprisingly been found out that the oil-in-water emulsion according to the present invention is highly effective in the treatment of excessive sweating and in particular of hyperhidrosis. In fact, quite unexpectedly the present invention allows for an improved release of the glycopyrronium salt from the emulsion being considered as one of the reasons for the improved efficacy. Moreover, the inventive emulsion provides both for an increased stability (i.e. stable emulsion without phase separation over time) and for a cosmetic acceptance leading to a well-balanced conveniently applicable product with favorable skin care characteristics. Also surprisingly, despite of the increased release of the glycopyrronium salts, the emulsion is free of side effects typical for common glycopyrronium compositions (i.e. local and systemic side effects, such as skin irritation or even inflammation at application site, application site pain, dry mouth, dry skin, dry eye, blurred vision, mydriasis, constipation, urinary hesitation, urinary retention, and nasal dryness). In the prior art it was not possible to sufficiently fulfill these properties all together at the same time.

Therefore, the present invention relates to an oil-in-water emulsion (also named O/W emulsion) comprising one or more glycopyrronium salts (also named glycopyrrolate or GP) and a specific emulsifier system. The emulsion preferably contains a disperse (inner) oil phase and a continuous (outer) water phase containing the glycopyrronium (GP) salt. Namely, the glycopyrronium salt due to its hydrophilic property and its water solubility is mainly contained in the water phase itself and in particular at the interface of the water and oil phases of the emulsion.

The oil phase of the O/W emulsion of the present invention may be a typical oil phase of O/W emulsions known in the prior art. Preferred as the main (basic) oil ingredient of the oil phase, however, are linear or branched long chain fatty alcohols having 6 to 36 carbon atoms, preferably having 6 to 22 carbon atoms. More preferably according to the present invention the oil phase contains octyldodecanol because of its skin smoothening and moisturizing effects and stability against oxidation even under acidic conditions (e.g. pH 4). Octyldodecanol further improves the permeation behaviour of the O/W emulsion of the present invention. Thus, the oil phase containing octyldodecanol is preferred because it provides improved skin care (e.g. smoothening and moisturizing) effects corresponding to an improved cosmetic acceptance of the patient or user.

The water phase comprises mainly water as solvent and the GP salt as active ingredient for treating hyperhidrosis. The water phase may also comprise water soluble/miscible compounds (e.g. lower alcohols such as ethanol or isopropanol), preservatives (such as benzyl alcohol or phenoxyethanol), pH adjusting agents or buffers (such as citric acid/citrate), as well as moisturizing agents (such as propylene glycol) and other typical hydrophilic pharmaceutical/cosmetic excipients.

The O/W emulsions of the present invention contain a smaller oil phase as compared to the water phase. Preferably the oil phase ranges from 10 to 25%, and the water phase ranges from 65 to 80 wt. % of the total weight of the emulsion. Despite of the relatively small ratio of the oil phase the emulsion of the invention surprisingly provides both for better stability (no phase separation) and for improved skin care characteristics, as already mentioned above. At the same time it was unexpected that the release rate of GP salts from the larger water phase was increased. Actually, the opposite was expected, namely a decreased release rate due to the larger water phase and the high water solubility and hydrophilic properties of GP salts. This allows for further reducing the amount of GP salts leading to a better side effect profile without reducing efficacy.

The glycopyrronium (GP) salts that may be used according to the present invention are not particularly limited, and any GP salts may be used. GP salts chemically mean (2-cyclopentyl-2-hydroxy-2-phenylacetyl)oxy]-1,1-dimethylpyrrolidinium salts. These include the chloride, bromide, fluoride, iodide, nitrate, sulfate, sulfonate, and phosphate salts of GP. Also suitable are the acetate, propionate, glycolate, pyruvate, oxalate, succinate, fumarate, tartrate, citrate, benzoate, methanesulfonate, 4-methylbenzenesulfonate (tosylate), and salicylate salts of GP. The emulsion of the invention may contain one, two, three or more different GP salts. However, preferably it contains only one GP salt. Particularly preferred GP salts are GP bromide (GPB), GP acetate and GP tosylate.

The GP salt according to the present invention may be any (2-cyclopentyl-2-hydroxy-2-phenylacetyl)oxy]-1,1-dimethylpyrrolidinium salt and in particular a racemic mixture of the (3R)-3-[(2S)-(2-cyclopentyl-2-hydroxy-2-phenylacetyl) oxy]-1,1-dimethylpyrrolidinium and (3S)-3-[(2R)-(2-cyclopentyl-2-hydroxy-2-phenylacetyl)oxy]-1,1-dimethylpyrrolidinium salts. Preferably a racemic mixture of (3R)-3-[(2S)-(2-cyclopentyl-2-hydroxy-2-phenylacetyl)oxy]-1,1-dimethylpyrrolidinium bromide and (3S)-3-[(2R)-(2-cyclopentyl-2-hydroxy-2-phenylacetyl)oxy]-1,1-dimethylpyrrolidinium bromide or a racemic mixture of (3R)-3-[(2S)-(2-cyclopentyl-2-hydroxy-2-phenylacetyl) oxy]-1,1-dimethylpyrrolidinium tosylate and (3S)-3-[(2R)-(2-cyclopentyl-2-hydroxy-2-phenylacetyl)oxy]-1,1-dimethylpyrrolidinium tosylate is used.

The oil-in-water emulsion according to the present invention may contain the GP salt, and in particular the GP bromide (GPB), in an amount of 0.05 to 5 wt. %, preferably of 0.1 to 3 wt. %, more preferably of 0.2 to 2 wt. %, and even more preferably of 0.5 to 1.5 wt. %, based on the weight of the total emulsion. When the GP salt, and in particular GPB, is contained in an amount within these ranges a high efficacy in reducing excessive sweating may be achieved while at the same time potential undesirable side effects of GP salts can be avoided. Furthermore, surprisingly a stable emulsion can be obtained even with high amounts of GP salt (namely even with 2 to 5 wt. % and in particular with 2 to 3 wt. %). Overall, an amount of about 1.0 wt. % GP salt (in particular GPB or GP tosylate, most preferably GPB) is most preferred especially from a cost, efficacy and side effect (safety) perspective.

The emulsifier system according to the present invention contains at least three different components, namely at least one macrogol glycerol fatty acid ester, at least one glycerol fatty acid ester, and at least one fatty alcohol. In the present application the term "macrogol", as common in the pharmaceutical field, is used as a synonym for "polyethylene glycol (PEG)". This is also supported by the skilled person's common general knowledge. Preferably, the emulsifier system comprises a combination of a macrogol glycerol fatty acid ester, a glycerol fatty acid ester, and a fatty alcohol. As the fatty alcohol it is preferred to use a mixture of two fatty alcohols. By using the specific emulsifier system in the O/W emulsion of the present invention the above mentioned effects (i.e. improved stability, increased release rate and efficacy, improved side effect profile and cosmetic acceptance/skin care characteristics) can be achieved.

More preferably with respect to the above described effects, the emulsifier system comprises a combination of macrogol glycerol monostearate, glycerol monostearate, and a mixture of cetyl alcohol and stearyl alcohol (e.g. with minimum 40.0 wt % stearyl alcohol). Even more preferably, the emulsifier system comprises a combination of macrogol 20 glycerol monostearate, glycerol monostearate 40-55, and cetostearyl alcohol. Cetostearyl alcohol is a mixture of fatty acid alcohols, in particular a mixture of cetyl and stearyl alcohols. Most preferably the emulsifier system (essentially) consists of these indicated combinations.

The oil-in-water emulsion according to the present invention may contain the respective components of the emulsifier system in the following amounts: 4.0 to 10.0 wt. %, preferably of 5.0 to 9.0 wt. %, more preferably of 6.0 to 8.0 wt. %, and even more preferably of 6.5 to 7.5 wt. % of the macrogol glycerol fatty acid ester; 1.5 to 7.5 wt. %, preferably of 2.5 to 6.5 wt. %, more preferably of 3.5 to 5.5 wt. %, and even more preferably of 4.0 to 5.0 wt. % of glycerol fatty acid ester; 5.0 to 11.0 wt. %, preferably of 6.0 to 10.0 wt. %, more preferably of 7.0 to 9.0 wt. %, and even more preferably of 7.5 to 8.5 wt. % of fatty alcohol, based on the weight of the total emulsion, respectively. By applying these preferred ranges the stability, cosmetic acceptance and efficacy is further improved.

The emulsifier system of the oil-in-water emulsion according to the present invention may contain the respective components in the following ratios: 21 to 51 wt. %, preferably of 26 to 46 wt. %, more preferably of 31 to 41 wt. %, and even more preferably of 33 to 38 wt. % of macrogol glycerol fatty acid ester; 8 to 38 wt. %, preferably of 13 to 33 wt. %, more preferably of 18 to 28 wt. %, and even more preferably of 21 to 26 wt. % of glycerol fatty acid ester; 26 to 56 wt. %, preferably of 31 to 51 wt. %, more preferably of 36 to 46 wt. %, and even more preferably of 38 to 44 wt. % of fatty alcohol (or fatty alcohol mixture), based on the weight of the emulsifier system, respectively. By applying these preferred ratios the stability, cosmetic acceptance and efficacy is further improved.

The oil-in-water emulsion of the present invention can be used as a pharmaceutical composition/medicament, as a medical device or as a cosmetic composition, depending on the indication to be treated and the respective regulatory requirements.

The compositions in accordance with the present invention may contain cosmetically and pharmaceutically/dermatologically acceptable excipients known to the skilled person. These include, next to the ones already mentioned above, for example further solvents such as organic solvents, gelling agents, buffers, detergents, emulsifiers, solubilizers, humectants, fillers, bioadhesives, emollients, preservatives, bactericides, surfactants, perfumes, thickeners, softening agents, moisturizing agents, oils, fats, waxes, water, alcohols, polyols, polymers, foam stabilizers, foaming agents, anti-foaming agents, hair coating agents or other suitable components of a pharmaceutical or cosmetic preparation.

Examples for bactericides are organic acids like formic acid, sorbic acid and benzoic acid. In addition esters of p-hydroxybenzoic acid, formaldehyde-releasing agents like DMDM hydantoin, imidazolidinylurea or methyl chloroisothiazolinone, methylisothiazolinone, dibromodicyanobutane, iodopropynyl butylcarbamate, phenoxyethanol or benzyl alcohol can be used as bactericides.

Further, pharmaceutically/dermatologically acceptable excipients according to the present invention may be inorganic or organic substances for topical administration. The pH value of the formulation can be stabilized using buffer systems consisting of polyacids and their salts. Examples for such polyacids are citric acid, tartaric acid and malic acid.

In the present invention, the emulsion is preferably a dermatological composition suitable to be applied topically on the skin of a mammal. The form of the composition is not particularly limited. In preferred embodiments, the compositions are in the form of lotions, creams, sprays, shampoos, foams, or saturated pads. Preferably they can be applied using a dispenser.

Clinical disorders/indications that may be treated with the emulsion of the invention generally are all indications associated with sweating, in particular excessive sweating. These include primary and secondary hyperhidrosis, gustatory sweating associated with Frey's syndrome, gustatory sweating associated with diabetic autonomic neuropathy, and excessive sweating in general. In particular, the following indications can be treated according to the present invention and are associated with dermatology, e.g. eccrine nevus, idiopathic unilateral focal hyperhidrosis, vascular deformities, pretibial myxedema; associated with gynaecology, e.g. postmenopausal hyperhidrosis; iatrogenic, such as associated with medicines, namely methadone or other opiates, cholinergics such as galantamine, SSRIs; associated with infection, e.g. brucellosis, HIV, chronic malaria, TBC, endocarditis; associated with surgery e.g. compensatory hyperhidrosis after sympathectomy; associated with medicines, such diabetes (hyperhidrosis due to neuropathy or hypoglycaemia), endocrine diseases (acromegaly, pheochromocytoma, hyperthyroidism, hypogonadism, insulinoma, heart failure, obesity); associated with neurology, e.g. central or peripheral lesion, Harlequin syndrome, Horner's syndrome, compensatory hyperhidrosis, Ross syndrome, Parkinson's disease, polyneuropathies; associated with oncology, such as carcinoid, lymphoma, with several malignancies; associated with orthopaedics, e.g. hyperhidrosis from amputation stump; associated with psychiatry, e.g. anxiety disorder, psychotropic drugs, social phobia.

Non-therapeutic (cosmetic) use of the oil-in-water emulsion of the present invention includes the topical application of the emulsion on the skin of a mammal in individuals who experience inconvenient sweating (i.e. both including ordinary sweating and/or excessive sweating).

The emulsion or composition of the present invention preferably is applied topically on the skin of a mammal. Typical application sites include the face (e.g. forehead, chin, neck and scalp), armpit, underarms, palms of the hands, soles of the feet, backs of the knees, trunk, and groin.

The emulsion or composition of the present invention preferably is topically applied onto the skin of a mammal 1-4 times a day, more preferably 1-2 times a day, even more preferably 1 time per day prior to bedtime, most preferably 2-3 times per week.

The following examples show preferred embodiments of the invention.

EXAMPLES

The following examples have been prepared by combining the indicated ingredients using a conventional mixer (e.g. Becomix RW 320). All ingredients are commercially available. Macrogol 20 glycerol monostearate is also known as polyethylene glycol (PEG)-20 glyceryl stearate. Glycerol monostearate 40-55 is also known as glycerol monostearate 40-55% (Type II). Cetostearyl alcohol is a mixture of cetyl and stearyl alcohols.

Preparation Example 1

| Position | Substance | g/100 g |
| --- | --- | --- |
| 1 | Macrogol 20 glycerol monostearate | 7.00 |
| 2 | Glycerol monostearate 40-55 | 4.50 |
| 3 | Cetostearyl alcohol | 8.00 |
| 4 | Octyldodecanol | 8.00 |
| 5 | Benzyl alcohol | 1.00 |
| 6 | Glycopyrronium bromide | 1.00 |
| 7 | Citric acid, anhydrous | 0.32 |
| 8 | Sodium citrate | 0.30 |
| 9 | Propylene glycol | 3.00 |
| 10 | Purified water | 66.88 |

Preparation Example 2

| Position | Substance | g/100 g |
| --- | --- | --- |
| 1 | Macrogol 20 glycerol monostearate | 7.00 |
| 2 | Glycerol monostearate 40-55 | 4.50 |
| 3 | Cetostearyl alcohol | 8.00 |
| 4 | Octyldodecanol | 8.00 |
| 5 | Benzyl alcohol | 1.00 |
| 6 | Glycopyrronium bromide | 0.50 |
| 7 | Citric acid, anhydrous | 0.32 |
| 8 | Sodium citrate | 0.30 |
| 9 | Propylene glycol | 3.00 |
| 10 | Purified water | 67.38 |

Preparation Example 3

| Position | Substance | g/100 g |
| --- | --- | --- |
| 1 | Macrogol 20 glycerol monostearate | 7.00 |
| 2 | Glycerol monostearate 40-55 | 4.50 |
| 3 | Cetostearyl alcohol | 8.00 |
| 4 | Octyldodecanol | 8.00 |
| 5 | Benzyl alcohol | 1.00 |
| 6 | Glycopyrronium bromide | 2.00 |
| 7 | Citric acid, anhydrous | 0.32 |
| 8 | Sodium citrate | 0.30 |
| 9 | Propylene glycol | 3.00 |
| 10 | Purified water | 65.88 |

All Preparation Examples exhibited a good stability of the O/W emulsions over 24 months during stability testing (stability of emulsion in terms of phase separation and in terms of stability of active pharmaceutical ingredient (API)).

A formulation preparation of Example 1 and the placebo formulation which had been stored at 30° C./75% RH for 18 months were stored at 5° C. or 50° C., respectively, for 3 d. Subsequently, samples were assessed regarding the parameters macroscopic and microscopic appearance, odour and viscosity. It was shown that short time storage of the formulations at 5° C. or 50° C. did not result in significant changes of odour, macroscopic and microscopic appearance. Minor changes in viscosity were observed with values within the specification.

Example—Treatment of Hyperhidrosis

Preparation samples according to the present application were tested in a clinical trial assessing pharmacokinetics, local and systemic tolerability and local efficacy of ascending concentrations of glycopyrronium bromide (GPB) in a topical formulation in a placebo controlled, double blind study in subjects with axillary hyperhidrosis.

The above Preparation Examples 1 to 3 containing 0.5 to 2.0 wt. % GPB were assessed for their efficacy in treating hyperhidrosis. They were topically applied once daily for 14 days on the skin of patients suffering from hyperhidrosis.

Exemplary results of Preparation Example 1 are as follows: The sweat production after one application was reduced up to 80%. In addition, reduction of sweat production after 7 days of treatment on day 8 was up to >95%. In the four point HDSS (hyperhidrosis disease severity scale) a two-point improvement was observed for >70% of patients on day 8 following 7 days of treatment. Such a high efficacy of a composition containing only 1.0 wt. % of GPB is evidence for a surprisingly increased release rate of GPB from the O/W emulsion of the present invention. This is because GPB due to its hydrophilic property and significant solubility in water it was actually expected to provide for a reduced release rate from the continuous (outer) water phase of the O/W emulsion.

Apart from the efficacy the emulsion of the present invention showed local excellent tolerability and mainly a local effect. In addition, the cosmetic acceptance of the O/W emulsion was high. The emulsion provides improved skin care characteristics including smoothening and moisturizing effects.

The invention claimed is:

1. An oil-in-water emulsion comprising at least one glycopyrronium (GP) salt and an emulsifier system, wherein the emulsifier system comprises:
   at least one macrogol glycerol fatty acid ester,
   at least one glycerol fatty acid ester, and
   at least one fatty alcohol;
   and wherein the at least one GP salt is a racemic mixture of (3R)-3-[(2S)-(2-cyclopentyl-2-hydroxy-2-phenylacetyl)oxy]-1,1-dimethylpyrrolidinium bromide and (3S)-3-[(2R)-(2-cyclopentyl-2-hydroxy-2-phenylacetyl)oxy]-1,1-dimethylpyrrolidinium bromide; or a racemic mixture of (3R)-3-[(2S)-(2-cyclopentyl-2-hydroxy-2-phenylacetyl)oxy]-1,1-dimethylpyrrolidinium tosylate and (3S)-3-[(2R)-(2-cyclopentyl-2-hydroxy-2-phenylacetyl)oxy]-1,1-dimethylpyrrolidinium tosylate.

2. The oil-in-water emulsion according to claim 1 comprising
   a) a disperse/inner oil phase;
   b) a continuous/outer water phase containing the glycopyrronium (GP) salt; and
   c) the emulsifier system.

3. The oil-in-water emulsion according to claim 1, wherein the at least one GP salt is present in an amount of 0.05 to 5 wt. %, based on the weight of the total emulsion.

4. The oil-in-water emulsion according to claim 1 comprising as the emulsifier system a combination of
   macrogol glycerol monostearate,
   glycerol monostearate, and
   a mixture of cetyl and stearyl alcohol with minimum 40.0 wt % stearyl alcohol.

5. The oil-in-water emulsion according to claim 1 comprising as the emulsifier system a combination of
   macrogol 20 glycerol monostearate,
   glycerol monostearate 40-55, and
   cetostearyl alcohol.

6. The oil-in-water emulsion according to claim 1 comprising
   an amount of 4.0 to 10.0 wt. % of the at least one macrogol glycerol fatty acid ester,
   an amount of 1.5 to 7.5 wt. % of the at least one glycerol fatty acid ester, and
   an amount of 5.0 to 11.0 wt. % of the at least one fatty alcohol,
   based on the weight of the total emulsion, respectively.

7. The oil-in-water emulsion according to claim 6 comprising an amount of 6.5 to 7.5 wt. % of the at least one macrogol glycerol fatty acid ester based on the weight of the total emulsion.

8. The oil-in-water emulsion according to claim 6 comprising an amount of 4.0 to 5.0 wt. % of the at least one glycerol fatty acid ester based on the weight of the total emulsion.

9. The oil-in-water emulsion according to claim 6 comprising an amount of 7.5 to 8.5 wt. % of the at least one fatty alcohol based on the weight of the total emulsion.

10. The oil-in-water emulsion according to claim 1, wherein the emulsifier system comprises
    an amount of 21 to 51 wt. % of the at least one macrogol glycerol fatty acid ester,
    an amount of 8 to 38 wt. % of the at least one glycerol fatty acid ester, and
    an amount of 26 to 56 wt. % of the at least one fatty alcohol,
    based on the weight of the emulsifier system.

11. The oil-in-water emulsion according to claim 1, wherein the at least one GP salt is present in an amount of 0.2 to 2 wt. %.

12. The oil-in-water emulsion according to claim 1, wherein the emulsifier system comprises an amount of 33 to 38 wt. % of the at least one macrogol glycerol fatty acid ester based on the weight of the emulsifier system.

13. The oil-in-water emulsion according to claim 1, wherein the emulsifier system comprises an amount of 21 to 26 wt. % of the at least one glycerol fatty acid ester based on the weight of the emulsifier system.

14. The oil-in-water emulsion according to claim 1, wherein the emulsifier system comprises an amount of 38 to 44 wt. % of the at least one fatty alcohol based on the weight of the emulsifier system.

15. A method for treating a clinical disorder comprising administering the oil-in-water emulsion according to claim 1 to a patient.

16. The method according to claim 15, wherein the clinical disorder to be treated is selected from the group consisting of primary and secondary hyperhidrosis, gustatory sweating associated with Frey's syndrome, gustatory sweating associated with diabetic autonomic neuropathy, and excessive sweating.

17. The method according to claim 15, wherein the emulsion is topically applied onto the skin of a mammal.

18. A pharmaceutical composition comprising the oil-in-water emulsion according to claim 1 and one or more pharmaceutically acceptable excipients.

19. A cosmetic composition comprising the oil-in-water emulsion according to claim 1 and one or more cosmetically acceptable excipients.

20. A method for reducing sweating in an individual comprising topically applying the cosmetic composition according to claim 19 on the skin of the individual.

* * * * *